(12) United States Patent
Hou et al.

(10) Patent No.: US 9,726,680 B2
(45) Date of Patent: Aug. 8, 2017

(54) REACTION VESSEL, ASSAY DEVICE, AND MEASURING METHOD

(71) Applicant: TAIDOC TECHNOLOGY CORPORATION, New Taipei (TW)

(72) Inventors: Hui-Sheng Hou, New Taipei (TW); Pin-Hsun Huang, New Taipei (TW); Chia-Chi Wu, New Taipei (TW)

(73) Assignee: TAIDOC TECHNOLOGY CORPORATION, New Taipei (TW)

( * ) Notice: Subject to any disclaimer, the term of this patent is extended or adjusted under 35 U.S.C. 154(b) by 946 days.

(21) Appl. No.: 14/073,048

(22) Filed: Nov. 6, 2013

(65) Prior Publication Data

US 2014/0127828 A1    May 8, 2014

(30) Foreign Application Priority Data

Nov. 7, 2012    (TW) .............................. 101141490 A

(51) Int. Cl.
*C12M 1/34*    (2006.01)
*G01N 33/72*    (2006.01)
*G01N 33/53*    (2006.01)
*B01L 3/00*    (2006.01)

(52) U.S. Cl.
CPC .......... *G01N 33/726* (2013.01); *B01L 3/5023* (2013.01); *G01N 33/5302* (2013.01); *G01N 33/723* (2013.01); *B01L 2200/10* (2013.01); *B01L 2200/16* (2013.01); *B01L 2300/022* (2013.01); *B01L 2300/087* (2013.01); *B01L 2400/0457* (2013.01); *B01L 2400/0683* (2013.01)

(58) Field of Classification Search
None
See application file for complete search history.

(56) References Cited

U.S. PATENT DOCUMENTS

| | | | | |
|---|---|---|---|---|
| 4,918,025 A | * | 4/1990 | Grenner | B01L 3/5027 422/565 |
| 4,990,075 A | * | 2/1991 | Wogoman | G01N 21/07 422/417 |
| 5,162,237 A | * | 11/1992 | Messenger | B01L 3/502 422/417 |
| 5,627,041 A | * | 5/1997 | Shartle | B01F 5/0604 422/50 |
| 7,497,997 B2 | * | 3/2009 | Glezer | B01J 19/0046 422/504 |
| 2011/0212453 A1 | * | 9/2011 | Agarwal | G01N 35/00029 435/6.12 |

* cited by examiner

*Primary Examiner* — Chris L Chin
(74) *Attorney, Agent, or Firm* — Chun-Ming Shih

(57) ABSTRACT

The present invention related to a reaction vessel and an assay device. A reaction vessel for analysis a sample containing an analyte to be determined, which includes a casing, a first reagent and at least one independent individual element. The casing includes an opening and a detection zone. The opening may be formed on the edge of the casing and used to introduce the sample. The detection zone is disposed at a corner of the casing and used to detect the analyte. The reagent is interacted with the sample. The independent individual element is individually separating from the casing and providing a space and a flow channel for mixing the sample and the first reagent. The sample and the reagent are mixed in the independent individual element so as to determine the analyte in the detection zone, and thereby increasing accuracy of analyte detection.

16 Claims, 16 Drawing Sheets

REACTION VESSEL, ASSAY DEVICE, AND MEASURING METHOD

BACKGROUND OF THE INVENTION

Field of the Invention

The present invention relates in general to a reaction vessel, an assay device and a measuring method, and particularly relates to a biochemical assay of the reaction vessel, the assay device and the measuring method.

Description of the Related Art

Conventional medical tests need to perform by the laboratory professionals' operation with a specific ratio of the reagent and the reaction time, and the process of medical test is usually complicated and time consuming. In order to comply with the call from the medical system for more rapid and convenient, a simple type of home-used medical devices have been developed.

Since many kinds of home-used medical devices have been developed, a biochemical reaction vessel with a reagent therein is one of them that have been extensively used for the blood tests or the urine tests, such as performing the tests related with the blood cells, the glycosylated hemoglobin, the urinary protein, the liver functional tests and so on. The test results of these biochemical reaction vessels are accurate which is closed to the accuracy of the results from the batch testing instruments in the hospital. The operation procedure of the home-used biochemical reaction vessels is relative simple and safety for the health care worker, and the time to obtain the test results is more rapid.

Currently, the design for the utilization way of the reaction vessel with the reagent therein is rotating the reaction vessel to a specific angle and controlling the reaction time of each different specific angle so as to perform the biochemical test analysis. However, the designs of the conventional reaction vessels have an issue that is having partial liquid residue in the casing while the test is performing, which is caused by pasting the top casing to the bottom casing to form at least a straight angle to let the liquid easily adhere, or pasting the casings to produce the excess glue where is the liquid easily adhered to. Besides, the flowing internal channels having the surface adhesion force for the liquid which is made by pasting the casings together will let the partial liquid be remained on the channel terminal or channel edge while the reaction vessel is rotating. That is hard to ensure that the predetermined volume of the reagents have been fully reacted, and further if it will affect the accuracy of the test results.

Therefore, there is an issue for manufacturer that how to further improve the deficiency described above.

SUMMARY OF THE INVENTION

According to one aspect of the present invention is to provide a reaction vessel for solving the liquid residual issue generated by right angle or excess glue made from work pieces adhering.

The present invention provides an assay device for preventing from flowing liquid residual on an edge of a channel terminal under operation process.

The present invention provides a measuring method for eliminating the deficiency caused by liquid residual so as to obtain more accurate test result.

In one aspect of the present invention, the present invention provides a reaction vessel for analysis a sample containing an analyte to be determined, which comprising a casing comprising an opening formed on the casing and used for introducing the sample; and a detection zone disposed at a corner of the casing and used for detecting the analyte;

a first reagent for mixing with the sample; and at least an independent individual element individually separating from the casing and providing a space and a flow channel for receiving the sample and the first reagent;

wherein the sample and the first reagent are mixed in the independent individual element, and the analyte is detected in the detection zone.

In an embodiment in accordance with the present invention, the independent individual element is adjacent to a side wall of the casing.

In an embodiment in accordance with the present invention, the reaction vessel further comprises a reservoir which comprises a body and a film. The film is used for letting the first reagent stored in the body in a sealed state, and the thickness of the reservoir is less than the opening of the casing, wherein one end of the reservoir is inserted in the independent individual element.

In an embodiment in accordance with the present invention, the independent individual element may be formed integrally and comprises a capacity zone, a flow channel and a distal end, and the capacity zone accommodates the sample and the first reagent which are mixed to form a first mixed liquid, and the flow channel is used for allowing the first mixed liquid flow through. The capacity zone may have a curved base, and an arc radius of the curved base is R1.0 to RN, in which N is a positive number larger than 1, and the flow channel may have an inclined plane with an inclined angle relative to a horizontal plan, which is between 30 degrees to 90 degrees.

In an embodiment in accordance with the present invention, the reaction vessel further comprises a second reagent for mixing with the first mixed liquid to form a second mixed liquid. Preferably, the first reagent is a liquid form and the second reagent is a dried form, and the sample is blood, and the viscosities of the first mixed liquid and the second mixed liquid are below 5 cP.

In an embodiment in accordance with the present invention, the reaction vessel further comprises a second independent individual element having a space and a flow channel for receiving the second mixed liquid, wherein the distal end of the independent individual element is inserted in the space of the second independent individual element.

In an embodiment in accordance with the present invention, the detection zone may be a transparent region to let a light transmit for detecting the analyte and the thickness of detection zone is 2 millimeter (mm) to 10 mm. The casing may further comprise a secured element and a limiting element. The secured element is engaged with the independent individual element to secure the independent individual element and prevent the independent individual element from shaking in the casing, and the limiting element cooperates with the secured element to limit the movement or shake of the independent individual element, and the reservoir is restricted by the limiting element with limitary shake.

In an embodiment in accordance with the present invention, the reaction vessel may further comprise a sampler which having a capillary tube used for drawing the sample. The reaction vessel may further comprise an absorptive material and a RFID tag. The absorptive material is adjacent to the detection zone and used for absorbing the sample and the reagent after interaction. The RFID tag is disposed on an outside of the casing and used for identifying a message related with the reaction vessel. The reaction vessel can be used for detecting a biochemical analyte and the biochemical analyte can be glycosylated hemoglobin.

In an embodiment in accordance with the present invention, the reaction vessel further comprises a tilted element to prevent the sampler from contacting an inner wall of the casing when the sampler is inserted into the casing.

In another aspect of the present invention, the present invention provides a method of manufacturing a reaction vessel, comprising:

providing at least two individual elements, and one of the individual elements with a solid reagent;

providing a reservoir comprising a body and a film, and the reservoir used for storing a liquid reagent in the body and sealed by the film;

providing a bottom casing having an opening for receiving a sample, and the bottom casing comprising a detection zone being a transparent region;

assembling the individual elements and the reservoir on the bottom casing; and adhering a top casing on the bottom casing to form the reaction vessel contained the at least individual elements and the reservoir.

In an embodiment in accordance with the present invention, the at least two individual elements are a first individual element and a second individual element, and the step between providing the at least two individual elements and providing the reservoir further comprises assembling the first individual element and the second individual element so as to form a communicated fluid channel between the first individual element and the second individual element.

In one another aspect of the present invention, the present invention provides a biochemical assay device for analysis a sample containing an analyte to be determined, which comprising:

a reaction vessel assembly comprising a sampler used for drawing the sample; and a reaction vessel comprising a casing comprising an opening and a detection zone, the opening formed on the casing and used for inserting the sampler, and the detection zone disposed at a corner of the casing and used for detecting the analyte;

a first reagent stored in a reservoir in a sealed state and used for mixing with the sample to form a first mixed liquid;

a second reagent used for mixing with the first mixed liquid to form a second mixed liquid;

a first independent individual element adjacent to a side wall of the casing and providing a space and a flow channel for the sample and the first reagent to be mixed to form the first mixed liquid; and a second independent individual element adjacent to an another side wall of the casing and receiving the second reagent and providing a space and a flow channel for the first mixed liquid and the second reagent to be mixed to form the second mixed liquid, wherein one end of the first independent individual element is inserted in the space of the second independent individual element; and a detecting instrument used for detecting the analyte in the reaction vessel assembly, and comprising a slot, a rotation element and a light detector, and the slot providing a space for inserting the reaction vessel assembly in the detecting instrument, and the rotation element rotating the reaction vessel assembly to let the sample, the first reagent and the second reagent mixed in the first independent individual element and the second independent individual element, and the light detector used for proceeding optical measurement so as to analyze the analyte concentration in the detection zone.

In one another aspect of the present invention, the present invention provides a method for biochemical reaction assay, comprising providing a reaction vessel comprising a sample, a first reagent and a first individual element, and the sample comprising an analyte;

rotating the reaction vessel to let the sample and the first reagent mix to form a first mixed liquid in the first individual element;

shaking the reaction vessel on an original point; and analyzing the analyte concentration.

In an embodiment in accordance with the present invention, the steps between shaking on the fixed point and analyzing the analyte concentration further comprise:

rotating the reaction vessel to let the first mixed liquid and a second reagent mix to form a second mixed liquid;

shaking the reaction vessel on an original point; and rotating the reaction vessel to let the second mixed liquid flow into a detection zone.

In an embodiment in accordance with the present invention, the analyte is glycosylated hemoglobin, and the analysis is optical measurement. A line perpendicular with a horizontal line is defined 0 degree so that rotating the reaction vessel 30 degrees to 55 degrees in clockwise direction is for mixing to form the first mixed liquid, and rotating the reaction vessel 50 degrees to 75 degrees in counterclockwise direction is for mixing to form the second mixed liquid, and rotating the reaction vessel 60 degrees to 85 degrees in clockwise direction is to let the second mixed liquid flow into the detection zone.

As used herein, the phrase "value R" means an arc radius and the phrase "arc of value R" means an arc drawn by the radius of the value. Preferably, the unit of value R is millimeter (mm).

As used herein, the phrase "individual element" means a capacity element with flow channel forming in one piece. The manufacturing of individual element can be either independently from the casing of reaction vessel or integrated with the casing of reaction vessel.

According to the aspect of the present invention as description above, the reaction vessel comprises at least an independent individual element having a flow channel forming in one piece, which decreases the liquid contacting surface of the casing. This can resolve the issue that partial liquid residual inappropriately remained at the edge of the casing which is caused by the casings pasting with each other to form a straight angle or the excess glue where the liquid easily attached. Furthermore, the independent individual element can pretreat with the reagent and individually save in an appropriate circumstance for the reagent so as to prolong the reagent efficiency and to elevate the accuracy of the test results.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF THE PREFERRED EMBODIMENTS

Figure 1A:
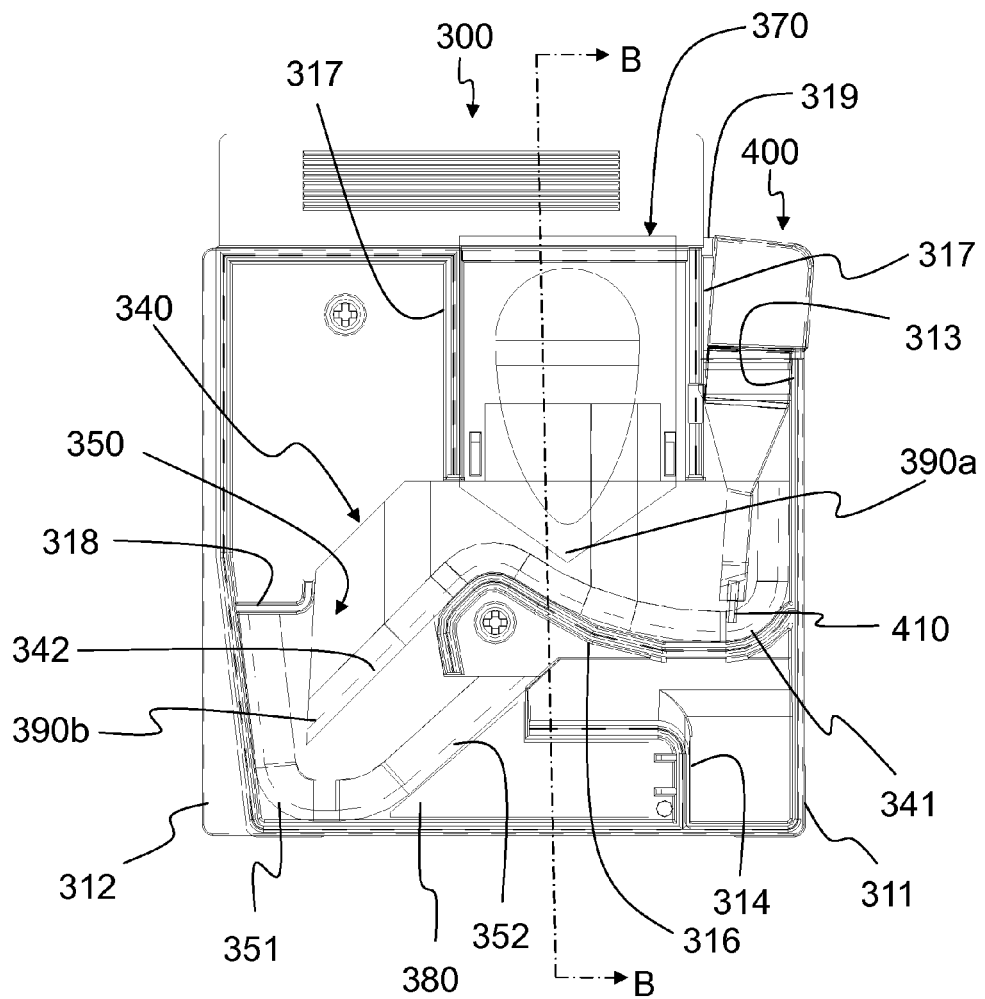
FIG. 1A is a schematic perspective view of a preferred embodiment of a reaction vessel assembly in accordance with the present invention.

For the purposes of promoting an understanding of the principles of the invention, reference will now be made to the embodiment illustrated in the drawings, and specific language will be used to describe that embodiment. It will nevertheless be understood that no limitation of the scope of the invention is intended. Alterations and modifications in the illustrated device, and further applications of the principles of the invention as illustrated therein, as would normally occur to one skilled in the art to which the invention relates are contemplated, are desired to be protected. Such alternative embodiments require certain adaptations to the embodiments discussed herein that would be obvious to those skilled in the art.

The following description and accompanying drawings are some examples in accordance with the present invention. The same symbol herein in the drawings indicates the same or similar structure.

Figure 1B:
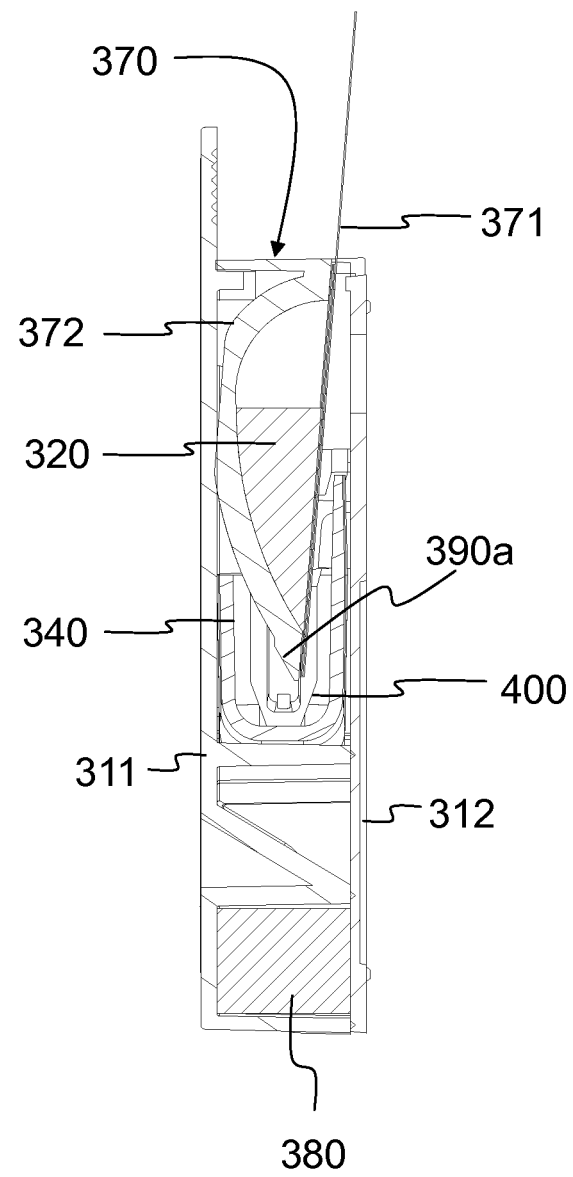
FIG. 1B is a cross-sectional view of B-B line of the reaction vessel assembly in FIG. 1A.

FIG. 1A is a schematic perspective view of a preferred embodiment of a reaction vessel assembly in accordance with the present invention. FIG. 1B is a cross-sectional view of B-B line of the reaction vessel assembly in FIG. 1A. Please refer to FIGS. 1A and 1B in combination. In accordance with the present embodiment, a reaction vessel assembly 30 used for detecting an analyte contained in a sample is provided, and the reaction vessel assembly 30 comprises a reaction vessel 300 and a sampler 400.

Figure 2A:
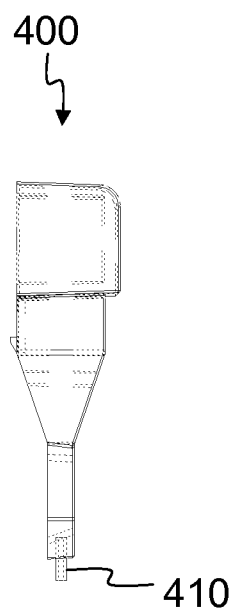
FIG. 2A is a schematic perspective view of a preferred embodiment of a sampler of the reaction vessel assembly in FIG. 1A in accordance with the present invention.
Figure 2B:
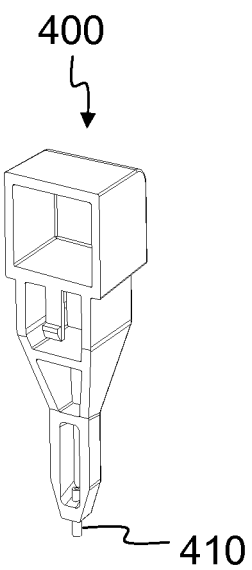
FIG. 2B is a schematic perspective view of another side of the sampler in FIG. 2A.

FIG. 2A is a schematic perspective view of a preferred embodiment of the sampler of the reaction vessel assembly in FIG. 1A in accordance with the present invention. FIG. 2B is a schematic perspective view of another side of the sampler in FIG. 2A in accordance with the present invention. Please refer to FIGS. 2A and 2B in combination. The sampler 400 further comprises a capillary tube 410. Preferably, the capillary tube 410 is disposed on an end of the sampler 400 for drawing a sample by capillarity from a tested subject. The sample can be a liquid sample, and the liquid sample preferably can be a biological liquid sample. The liquid sample can be obtained from human body such as blood, urine, plasma, serum, cerebro-spinal fluid (CFS), spinal fluid or other body fluid. An analyte is contained in the sample, such as blood cell, glycosylated hemoglobin, urinary protein or other test targets about liver function. In other words, in accordance with the other embodiment, the sample can contain one or more than one kinds of analytes.

Figure 3:
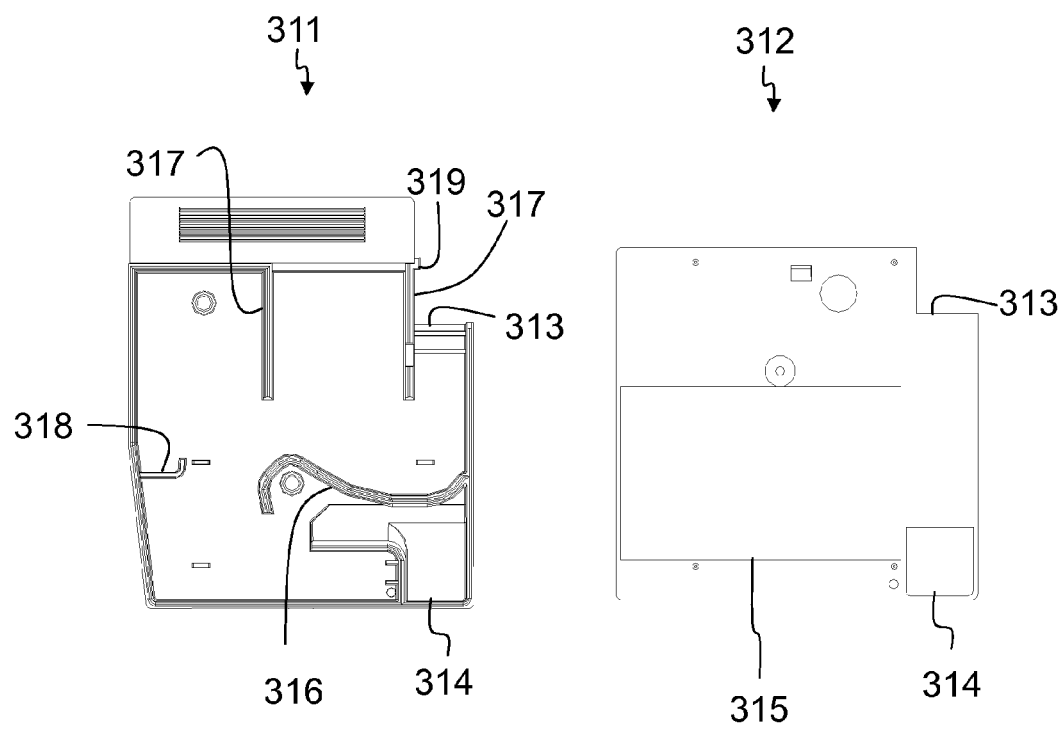
FIG. 3 is an exploded schematic perspective view of a preferred embodiment of a casing of the reaction vessel in FIG. 1A in accordance with the present invention.

FIG. 3 is an exploded schematic perspective view of a preferred embodiment of a casing of the reaction vessel in FIG. 1A in accordance with the present invention. Please refer to FIG. 3 in combination. The reaction vessel 300 comprises a casing 310, a first reagent 320 and at least one independent individual element. In a preferred embodiment of the present invention, the casing is constituted by a bottom casing 311 and a top casing 312, and has an opening 313 and a detection zone 314. The opening 313 is formed on the casing and used for introducing the sample. Preferably, the opening 313 can be formed on an edge of the casing 310. Preferably, the sample is drawn by the capillary tube 410 of the sampler 400, and then the sampler 400 is inserting to the opening 313 of the casing 310. In another preferred embodiment of the present invention, the opening 313 can be formed on a corner of the casing 310. The detection zone 314 is used for detecting the analyte in the sample, and disposed on the other corner of the casing 310. Preferably, the detection zone 314 is a transparent region to let a light transmit for detecting the analyte. The thickness of the detection zone is 2 millimeter (mm) to 10 mm which is a distance for the light transmission path.

In a preferred embodiment of the present invention, the casing 310 further comprises a radio frequency identification (RFID) tag 315 used for identifying a message related with the reaction vessel 300 such as the manufacturing parameters used for detecting the analyte, the analyte category, the patient identification, and so on. Preferably, the RFID tag 315 is disposed on an outside of the top casing 312.

Figure 4A:
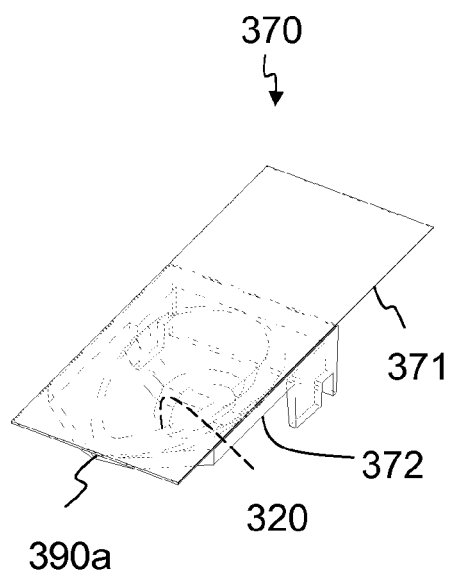
FIG. 4A is a schematic perspective view of top side of a preferred embodiment of a reservoir of the reaction vessel in FIG. 1A in accordance with the present invention.
Figure 4B:
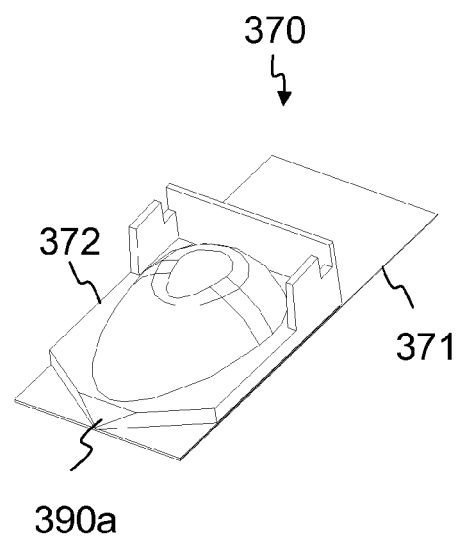
FIG. 4B is a schematic perspective view of another side of the reservoir in FIG. 4A.

FIG. 4A is a schematic perspective view of top side of a preferred embodiment of a reservoir of the reaction vessel in FIG. 1A in accordance with the present invention. FIG. 4B is a schematic perspective view of another side of the reservoir in FIG. 4A. Please refer to FIGS. 4A and 4B in combination. The reaction vessel 300 further comprises a reservoir 370 used for storing the first reagent 320 in a sealed state. The reservoir 370 has a film 371 and a body 372, and the body has a distal end 390a. Preferably, a storage space of the body 372 which is storing the first reagent 320 is an elliptical tank and the film is an aluminum foil. The distal end 390a is inserted in the independent individual element. The thickness of the reservoir 370 is less than the opening 313 of the casing preferably.

Figure 10A:
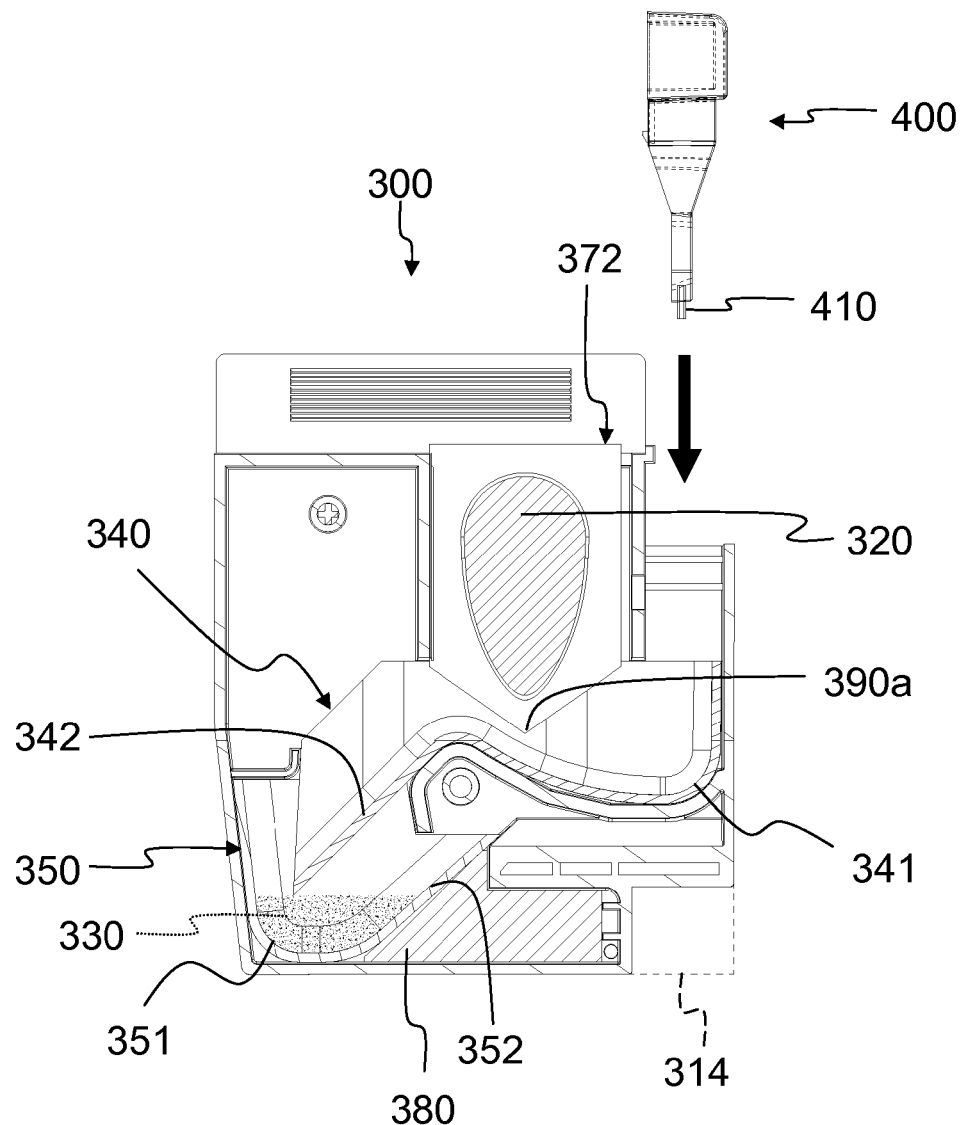
FIGS. 10A to 10E are schematic perspective views of operation process in accordance with the flow chart in FIG. 9 in accordance with the present invention. In these Figures, a top casing and a film of the reservoir are not shown, and the boldface arrowhead with solid line is pointed the direction of the sampler movement or the reaction vessel rotation, and the boldface arrowhead with dotted line pointed the direction of liquid flow.
Figure 10B:
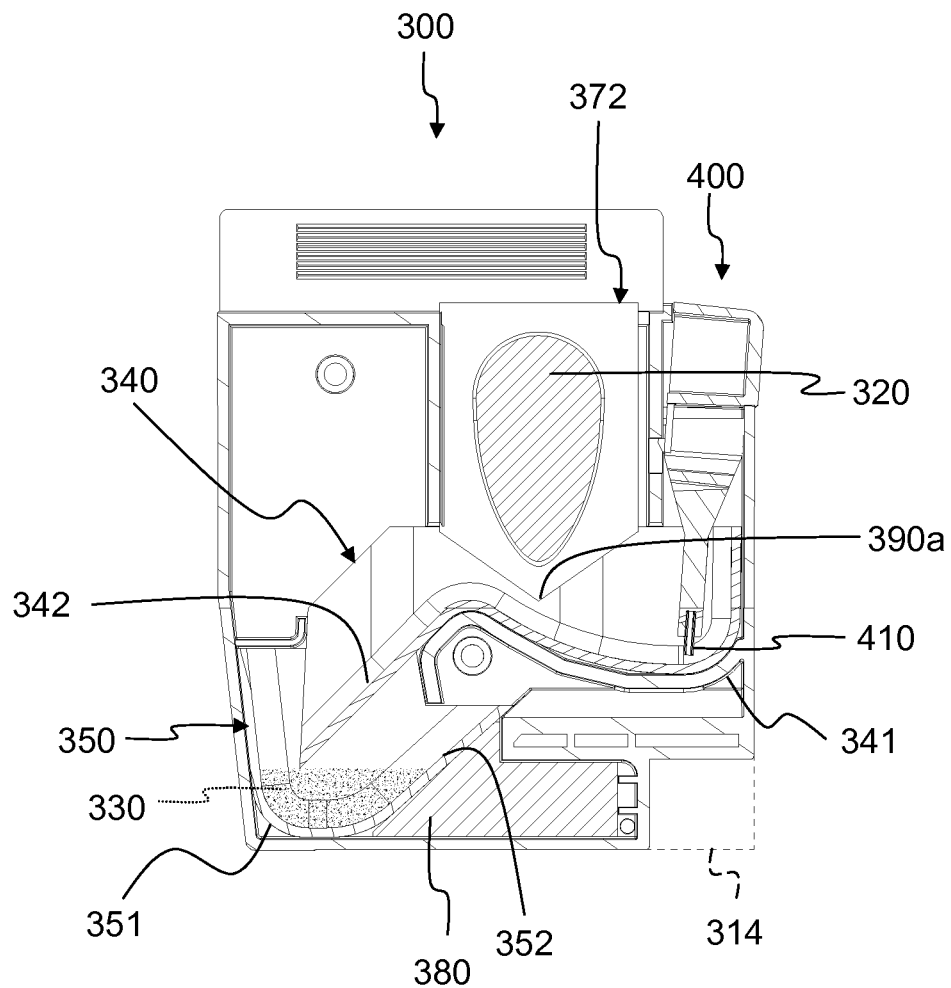
Figure 10C:
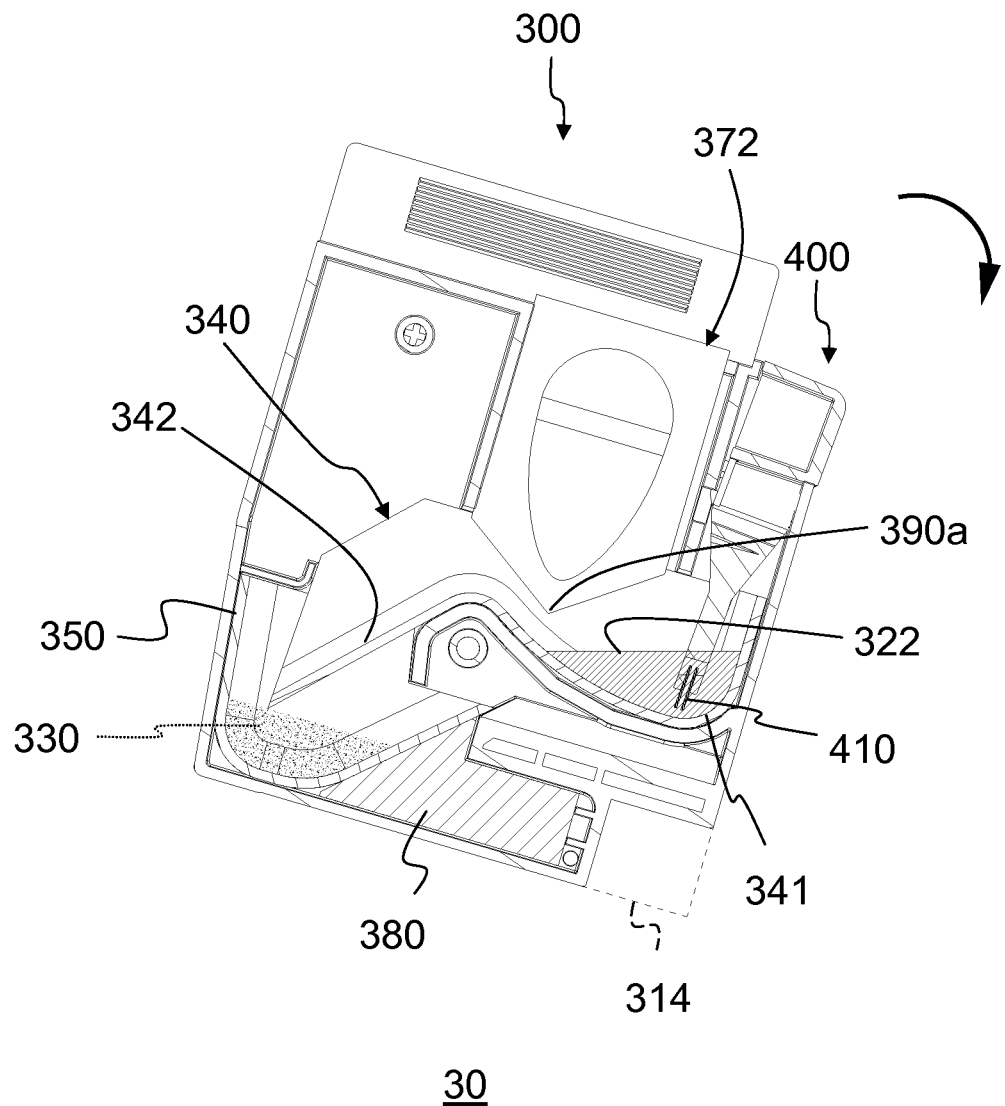

The first reagent 320 is mixing with the sample to form a first mixed liquid 322 (please refer to FIG. 10C which will be described later). The first reagent 320 can be a liquid form. Preferably, the first reagent 320 comprises a hemolytic reagent stored in the reservoir 370. More specifically, the film 371 seals the first reagent 320 within the body 372 of the reservoir 370. When the sample introduced in the reaction vessel 300, the film 371 will be pulled off to let the first reagent 320 leave from the body 372 and pass through the distal end 390a of the reservoir 370 and then mixing with the sample in the independent individual element. The reaction vessel 300 further comprises a second reagent which is mixing with the first mixed liquid 322 to form a second mixed liquid 332 (please refer to FIG. 10D which will be described later), but the present invention shall not be limited for this. Either the number or the species of the first reagent and the second reagent can vary corresponding with the analyte that need to be determined. The second reagent can be a dried form which is made by the manufacturing process of freezing and drying the liquid type reagent, but the present invention shall not be limited in this. Preferably, the second reagent comprises an immune reagent. More specifically, the mixing reaction is a biochemical reaction. Preferably, the biochemical reaction can be an immunological agglutination. In a preferred embodiment of the present invention, the viscosities of the first mixed liquid 322 and the second mixed liquid 332 in the reaction vessel 300 are below 5 centipoise (cP).

Following the description above, the reaction vessel 300 comprises at least one independent individual element which comprises a space and a flow channel for receiving the sample and the first reagent. More specifically, the space which meaning a capacity zone and the flow channel of the independent individual element are formed integrally and made by plastic material. The plastic material can be a hydrophobic material or the plastic material which has been doing a hydrophobic process. Preferably, the hydrophobic plastic material can be a thermoplastic such as polypropylene (PP), polymethylmethacrylate (PMMA) and so on. In accordance with the other embodiment, those skilled in the art can change the plastic material of used in the manufacturing process as needed.

Figure 5A:
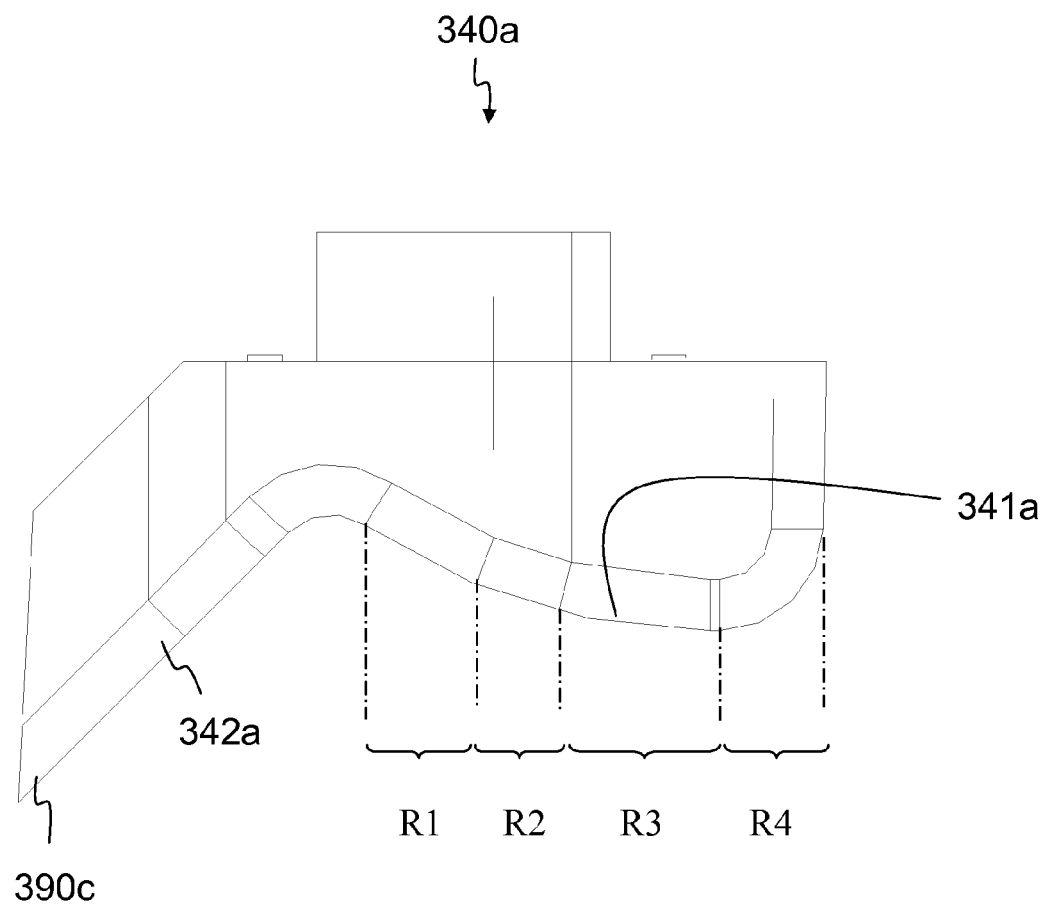
FIG. 5A is an enlarged lateral side schematic perspective view of a preferred embodiment of an independent individual element of the reaction vessel in accordance with the present invention.

FIG. 5A is an enlarged lateral side schematic perspective view of a preferred embodiment of the independent individual element of the reaction vessel in accordance with the present invention. Please refer to FIG. 5A. In a preferred embodiment of the present invention, the independent individual element 340a comprises a capacity zone 341a, a flow channel 342a and a distal end 390c, and the capacity zone 341a comprises a curved base. More specifically, in accordance with the present embodiment, the shape of the curved base is an arc shape drawn by the radius of a value R. Preferably, the unit of value R is millimeter (mm). For example, value R1.0 of the arc shape of the curved base means the arc is drawing by the radius of 1.0 mm. Preferably, the arc radius of the curved base is between R1.0 to RN, in which N is a positive number larger than 1. More preferably, the arc radius of the curved base is between R4.0 to R40.0. To be noticed, the arc radius of curved base in the capacity zone 341a is not being limited with a single numerical value R. In other words, those skilled in the art can change the shape of the curved base by modifying the arc of the capacity zone 341a to determine the width of the curved base or the height of accommodated liquid which is decided based on the casing size of the reaction vessel, the liquid pathway or other design demand as needed. For example, as FIG. 5A shown, R1 to R4 are indicating four different values of the arc radius, and the curved base of the capacity zone 341a is composed by the arc shape of R1 to R4. More specifically, those skilled in the art can decide to use more than one numerical value R of the arc radius to modify the shape of the curved base of the capacity zone 341a.

The flow channel 342a is an integrally formed channel used for fluid communication with the capacity zone 341a in the independent individual element 340a, and the flow channel 342a preferably has an inclined plane. More specifically, the inclined plane has an inclined angle relative to a horizontal plan. The horizontal plan is defined 0 degree, and the inclined angle preferably can be 30 degrees to 90 degrees.

The distal end 390c is a terminal end of the flow channel of the individual element, where is a place perhaps having an issue with residual liquid. In a preferred embodiment of the present invention, the sample is mixed with the first reagent in the independent individual element to form a first mixed liquid and then the first mixed liquid flows into the detection zone 314 for detecting the analyte in the sample.

Figure 5B:
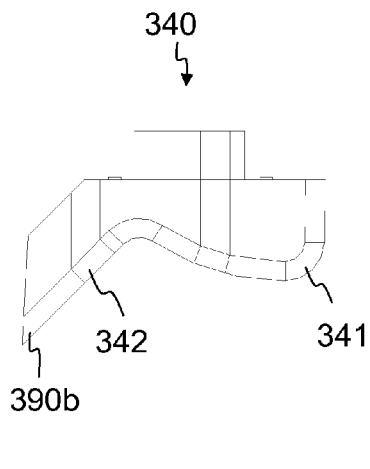
FIG. 5B is a schematic perspective view of a preferred embodiment of a first independent individual element of the reaction vessel in FIG. 1A in accordance with the present invention.
Figure 5C:
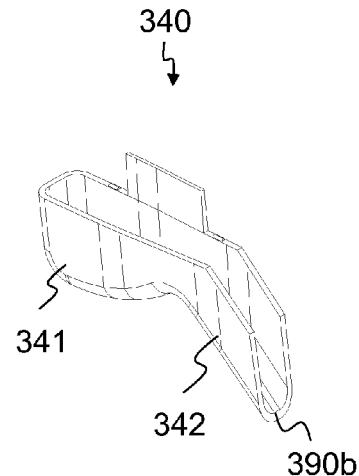
FIG. 5C is a schematic perspective view of another side of the first independent individual element in FIG. 5B.
Figure 5D:
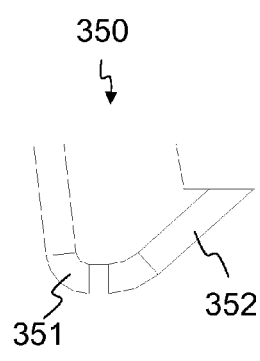
FIG. 5D is a schematic perspective view of a preferred embodiment of a second independent individual element of the reaction vessel in FIG. 1A in accordance with the present invention.
Figure 5E:
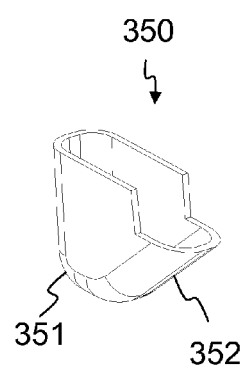
FIG. 5E is a schematic perspective view of another side of the second independent individual element in FIG. 5D.

FIG. 5B is a schematic perspective view of a preferred embodiment of a first independent individual element of the reaction vessel in FIG. 1A in accordance with the present invention. FIG. 5C is a schematic perspective view of another side of the first independent individual element in FIG. 5B. FIG. 5D is a schematic perspective view of a preferred embodiment of a second independent individual element of the reaction vessel in FIG. 1A in accordance with the present invention. FIG. 5E is a schematic perspective view of another side of the second independent individual element in FIG. 5D. Please refer to FIGS. 5B and 5E in combination. In a preferred embodiment of the present invention, the independent individual element further comprises a first independent individual element 340 and a second independent individual element 350, and the first independent individual element 340 is fluid communication with the second independent individual element 350. The first independent individual element 340 is adjacent to a side wall of the casing 310 and used for providing a space and a flow channel 342 for the first mixed liquid 322 (please refer to FIG. 10C which will be described later). More specifically, the sample is mixed with the first reagent 320 in the capacity zone 341 of the first independent individual element 340 then flowing through the flow channel 342 into the second independent individual element 350. In a preferred embodiment of the present invention, the capillary tube 410 of the sampler 400 and the distal end 390a of the reservoir 370 are inserted in the capacity zone 341 of the first independent individual element 340. Therefore, the first reagent 320 stored in the reservoir 370 flows to the capacity zone 341 to bring the sample out from the capillary tube 410 then mixed to form the first mixed liquid 322. The second independent individual element 350 is adjacent to an another side wall of the casing 310 and used for providing a space and a flow channel 352 for the second mixed liquid 332 (please refer to FIG. 10D which will be described later). Preferably, a second reagent (not shown) is disposed in the capacity zone 351 of the second individual element 350. The second reagent can be a liquid form or a dried form, wherein the dried form of the second reagent can be made by putting the liquid form of the second reagent in the second independent individual element 350 and then performing the freeze drying procedure to let the second reagent be a dried solid state and attach on the inner wall of the second independent individual element 350. More specifically, the first mixed liquid 322 from the first independent individual element flowing through the flow channel 342 into the second independent individual element 350 is mixed with the second reagent to form the second mixed liquid 332. In a preferred embodiment of the present invention, the distal end 390b of the first independent individual element 340 can engage with the capacity zone 351 of the second independent individual element 350 to form a fluid communication state which can let the first mixed liquid 322 flow into the capacity zone 351 of the second independent individual element 350. In other words, the independent individual element has an integrated flow channel formed in one piece therefore decreasing the surface area that is the liquid contacted with in the casing. Therefore, the independent individual element can prevent the problem about the residual liquid attached on the casing surface while test performing which is caused by the straight angles and/or the excess glue formed from the reaction vessel casings pasting with each other. In addition, the pretreatment reagent coating in the independent individual element has an advantage that could separately save in an appropriate circumstance from the reaction vessel so as to prolong the efficiency of the reagent.

Please refer to FIGS. 1A and 1B in combination. The casing 310 of the reaction vessel 300 further comprises a secured element engaged with the independent individual element to secure the independent individual element and prevent the independent individual element from shaking in the casing 310. In a preferred embodiment of the present invention, the secured element comprises a first secured element 316 and a second secured element 318. The first secured element 316 is engaged with the first independent individual element 340 and the second independent individual element 350 for securing the first independent individual element 340 and the independent second individual element 350 in the casing 310, and the second secured element 318 is engaged with the second independent individual element 350 for securing the second independent individual element 350 in the casing 310. Preferably, the first secured element 316 is a curved sheet to hold the first independent individual element 340 and the shape of the first secured element 316 is fitted with the bottom side of the first independent individual element 340. The first secured element 316 is extended from a side wall of the casing 310 toward the inside of the casing 310, and a terminal of the first secured element is fastened with one side of the second independent individual element. The second secured element 318 is disposed inside the casing 310 and corresponding to the other side of the second independent individual element 350 for limiting the wobble or movement of the second independent individual element 350.

Furthermore, the casing 310 of the reaction vessel 300 further comprises a limiting element 317 used for cooperating with the first secured element 316 to limit the movement or shake of the first independent individual element 340 and the reservoir 370 is restricted by the limiting element with limitary shake. Preferably, the limiting element 317 is disposed at two relative sides of the reservoir 370. The embodiment described above is one choice of an embodiment of the present invention. In accordance with the other embodiment, the first secured element can be any type structures to fasten the first independent individual element, such as using plural columns rather than the sheet structure, but the present invention shall not be limited for this.

Besides, in a preferred embodiment of the present invention, the reaction vessel 300 further comprises an absorptive material 380 adjacent to the detection zone 314 and used for absorbing the sample and the first reagent after interaction, and the absorptive material preferably can be a sponge. After the sampler 400 was inserted into the reaction vessel 300, the sample is mixed with the first reagent, then the analyte contained in the sample is detected at the detection zone 314. Finally, the sample will be absorbed after reaction by the absorptive material 380.

In a preferred embodiment of the present invention, the reaction vessel 300 further comprises a tilted element 319 to prevent the sampler 400 from contacting an inner wall of the casing 310 when the sampler is inserted to the casing 310. In accordance with the present embodiment, the tilted element 319 is a block next to the opening 313 and protruded from the side wall of the casing, but the present invention shall not be limited for this. In accordance with the other embodiment, the tilted element can be any designs to prevent the sampler 400 from contacting the inner wall of the casing 310, for example, the tilted element 319 can be disposed on the sampler 400.

Figure 6:
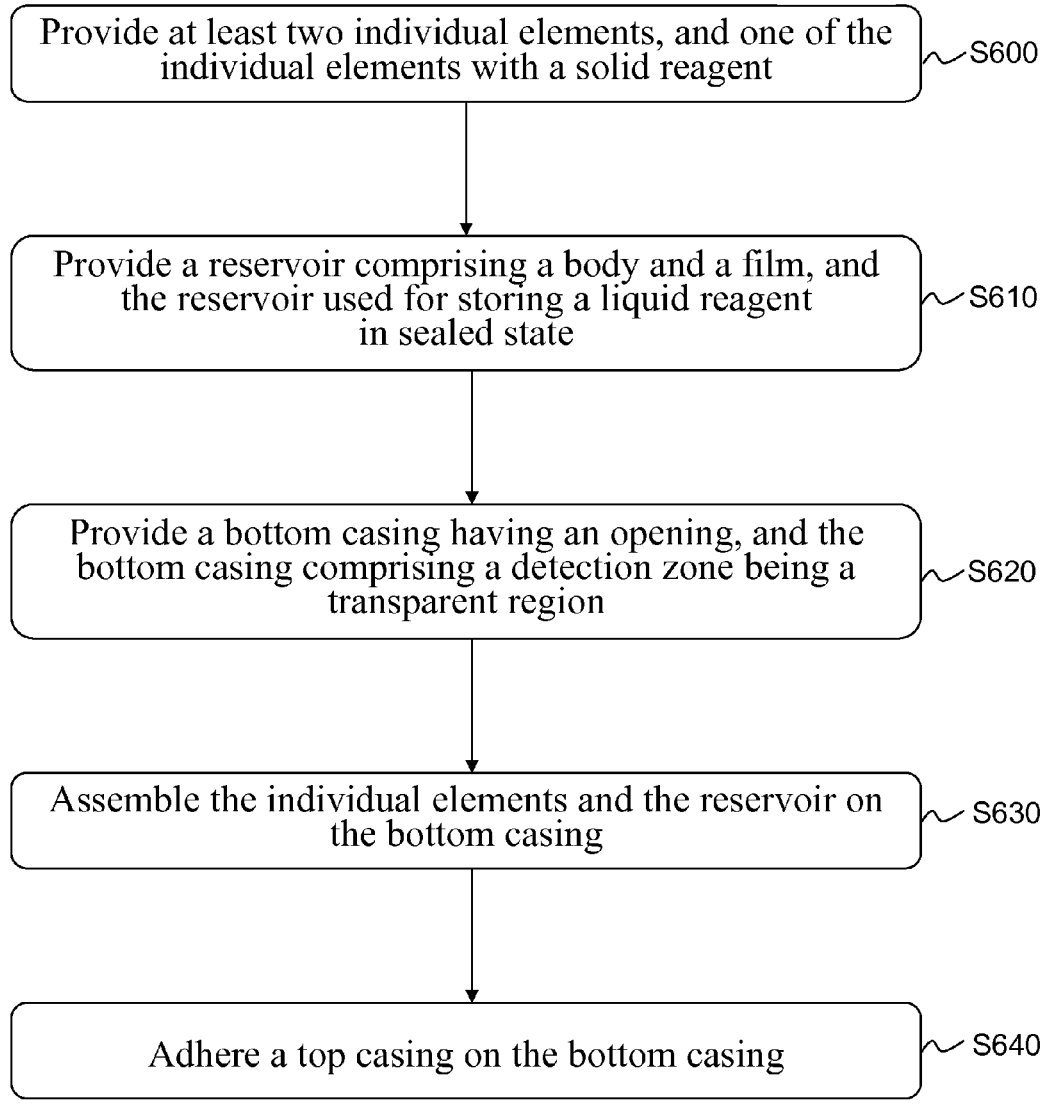
FIG. 6 is a flow chart of a preferred embodiment of a method of manufacturing a reaction vessel in accordance with the present invention.

FIG. 6 is a flow chart of a preferred embodiment of a method of manufacturing a reaction vessel in accordance with the present invention. Please refer to FIGS. 3 to 6 and FIG. 1A in combination. In a preferred embodiment of the present invention, provide at least two independent individual elements, and one of the independent individual elements with a solid reagent in step S600. In other words, the two independent individual elements can be the first independent individual element 340 and the second independent individual element 350. Preferably, the second reagent in a dried form is disposed in the second independent individual element 350. In accordance with the present embodiment, preferably assemble the first independent individual element 340 and the second independent individual element 350 to let the distal end 390b of the first independent individual element 340 put into the capacity zone 351 of the second independent individual element 350 so that the flow channel 342 of the first independent individual element 340 is cooperated with the flow channel 352 of the second independent individual element 350 to form a fluid communication channel. In step S610, provide a reservoir comprising a body and a film, and the reservoir is used for storing a liquid reagent in a sealed state. In other words, the film 371 is used to seal the liquid reagent within the body 372, and the liquid reagent preferably is the first reagent. Following the step S620, provide a bottom casing 311 which is having an opening 313, and the bottom casing 311 comprises a detection zone 314 which is a transparent region for light transmission so as to detect the analyte by optical measurement. Following the step S630, assemble the independent individual elements and the reservoir on the bottom casing. More specifically, there is a space of the bottom casing 311 for engaging the independent individual elements and the reservoir 370 in the reaction vessel 300. Following the step S640, adhere a top casing 312 on the bottom casing 311, and the method for adhering the casings preferably can be colloidal adhesion or ultrasonic welding.

Figure 7:
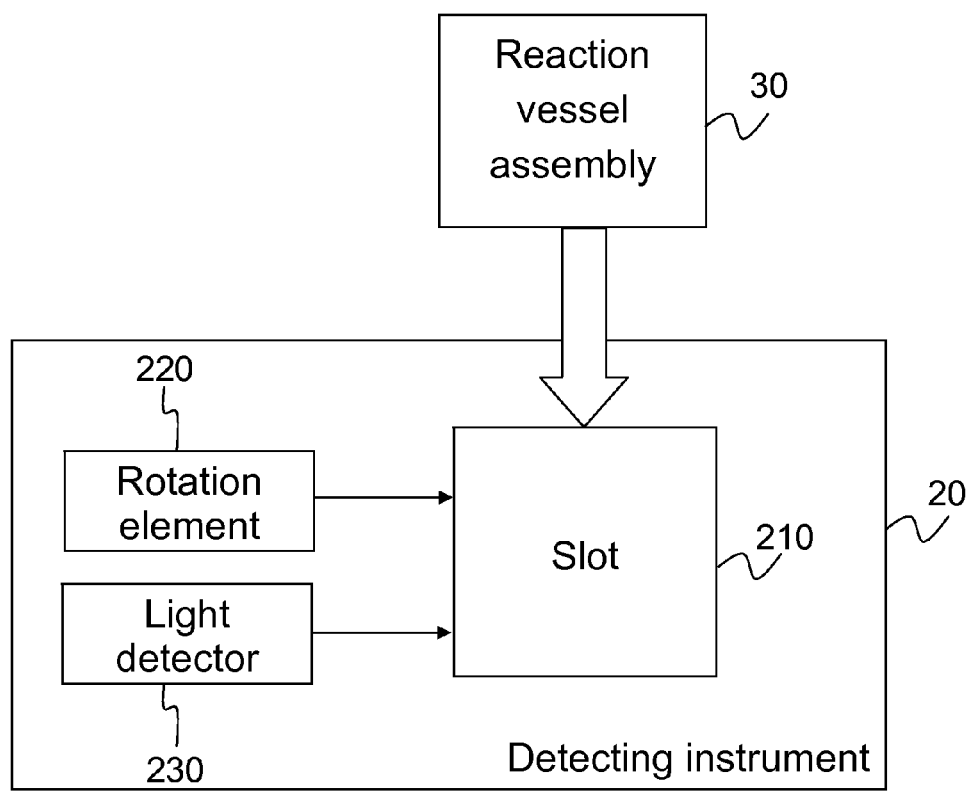
FIG. 7 is a block diagram of a preferred embodiment of a detecting instrument in accordance with the present invention.

FIG. 7 is a block diagram of a preferred embodiment of a detecting instrument in accordance with the present invention. Please refer to FIG. 7. In a preferred embodiment of the present invention, a biochemical assay device 10 for detecting an analyte contained in a sample, which comprises a reaction vessel assembly 30 and a detecting instrument 20. The reaction vessel assembly 30 comprises a sampler 400 and a reaction vessel 300. The detecting instrument 20 comprises a slot 210, a rotation element 220 and a light detector 230. The slot 210 provides a space for inletting the reaction vessel assembly 30 in the detecting instrument 20. The rotation element 220 is used for rotating the reaction vessel assembly 30 so as to mix the sample, the first reagent and the second reagent in the casing 310. More specifically, the rotation element 220 can provide clockwise or counterclockwise rotation, or shake the reaction vessel assembly 30 on an original point. The light detector 230 is used for optical measurement so as to analyze the analyte concentration in the detection zone 314. Preferably, the optical measurement can be transmission type or reflection type.

Figure 8:
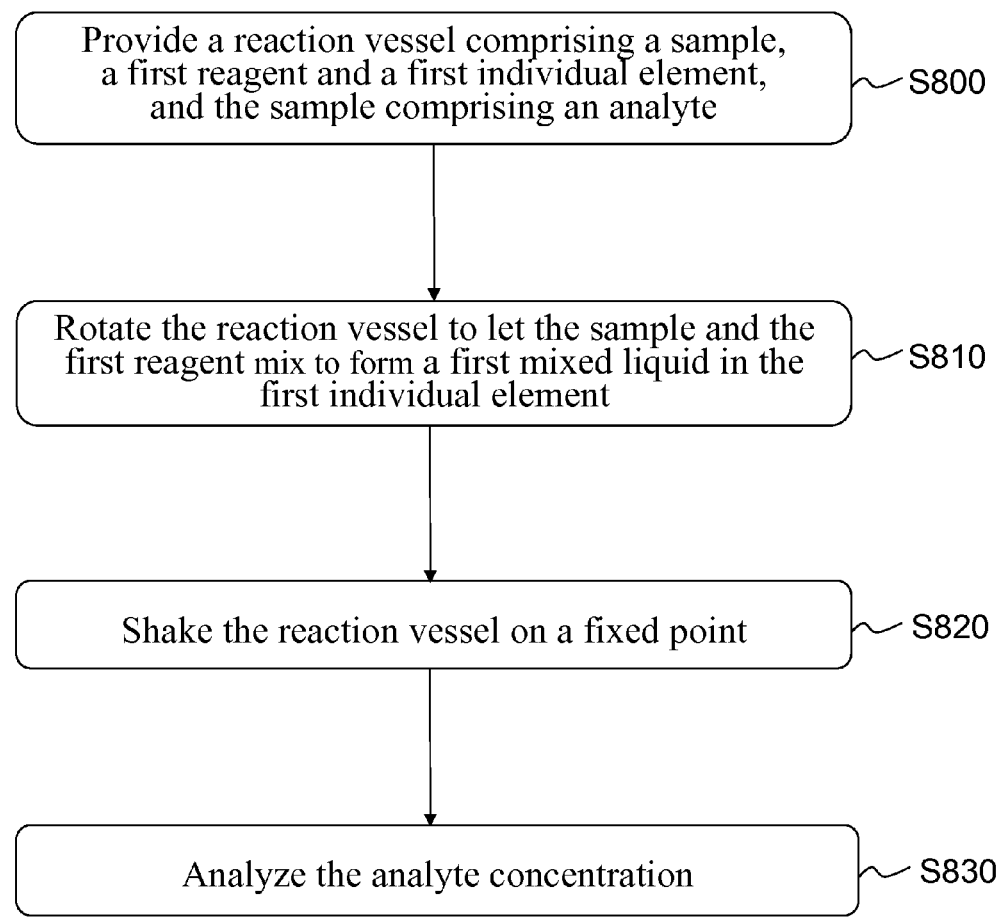
FIG. 8 is a flow chart of a preferred embodiment of a method for biochemical reaction assay in accordance with the present invention.

FIG. 8 is a flow chart of a preferred embodiment of a method for biochemical reaction assay in accordance with the present invention. Please refer to FIG. 8. In a preferred embodiment of the present invention, provide a reaction vessel for detecting an analyte contained in a sample and comprising a first reagent and a first independent individual element in step S800. Preferably, the sample and the first reagent are in liquid form and the first independent individual element has a capacity zone. Following the step S810, rotate the reaction vessel for mixing the sample and the first reagent to form a first mixed liquid in the first independent individual element. More specifically, the rotation can be a clockwise or counterclockwise rotation. Following the step S820, shake the reaction vessel at an original point. More specifically, after rotating a specific angle of the reaction vessel in the step S810, set that point to be an original point for slightly shaking clockwise and counterclockwise alternately so as to let the sample and the first reagent 320 completely react. Following the step S830, analyze the analyte concentration. The analysis preferably can be an optical measurement, but the present invention shall not be limited for this. Those skilled in the art can change the rotation times which is according to the different kinds of the reagent or the analyte numbers to be determined as needed.

Figure 9:
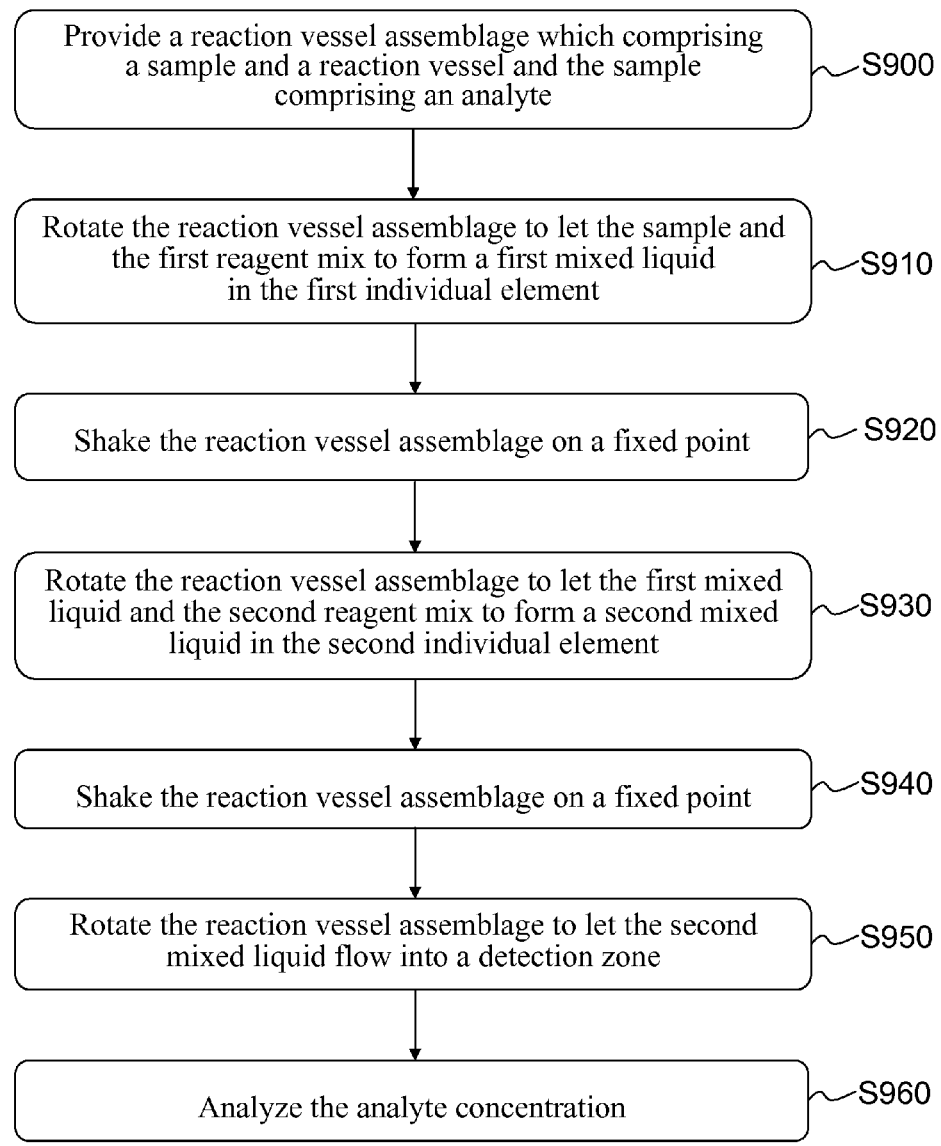
FIG. 9 is a flow chart of another preferred embodiment of a method for biochemical reaction assay in accordance with the present invention.

FIG. 9 is a flow chart of another preferred embodiment of a method for biochemical reaction assay in accordance with the present invention. FIGS. 10A to 10E are schematic perspective views of operation process in accordance with the flow chart of a preferred embodiment of a method for biochemical reaction assay in FIG. 9 in accordance with the present invention. In these Figures, the top casing and the sealed film of the reservoir are not shown, and the boldface arrowhead of the solid line is pointing out the direction of the sampler movement or the direction of the reaction vessel rotation, and the boldface arrowhead of the dotted line is pointing out the direction of the liquid flow. Please refer to FIGS. 9 and 10D in combination. In a preferred embodiment of the present invention, provide a reaction vessel assembly 30 for detecting an analyte contained in a sample and comprising a reaction vessel 300 in step S900. Preferably, the sample is liquid form which drawing by a capillary tube 410 of a sampler 400 then introducing in the reaction vessel 300 (as FIGS. 10A and 10B shown). The reaction vessel 300 comprises a casing 310, a first reagent 320, a second reagent 330, a first independent individual element 340 and a second independent individual element 350. The casing 310 comprises an opening 313 and a detection zone 314. The opening 313 is formed on the edge of the casing 310 for inletting the sampler 400, and the detection zone 314 is used for detecting the analyte. The first reagent 320 is mixed with the sample to form a first mixed liquid 322, and preferably, the first reagent 320 is stored in a reservoir 370. The reservoir 370 comprises a film 371 and a body 372 which having a distal end 390a, and the thickness of the reservoir 370 is less than the opening 313 of the casing. The second reagent 330 is mixed with the first mixed liquid 322 to form a second mixed liquid 332, and preferably, the second reagent 330 is disposed in the second independent individual element 350. The first independent individual element 340 provides a space and a flow channel 342 for mixing the sample and the first reagent 320 to form the first mixed liquid 322. The second independent individual element 350 provides a space and a flow channel 352 for mixing the first mixed liquid 322 and the second reagent 330 to form the second mixed liquid 332.

According to the aspect of the present invention as described above, preferably pull off the film 371 from the reservoir 370 to let the first reagent 320 leave from the body 372 and passing through the distal end 390a of the reservoir 370 into the first independent individual element 340. At this time, the liquid level of first reagent 320 in the first independent individual element 340 is higher than the capillary tube 410 of the sampler 400 accommodated in the first independent individual element 340, and the liquid volume of the first reagent 320 is sufficient to release the sample in the capillary tube 410. To be noticed, the sampler 400 does not completely contact with the inner wall of the casing 310 to prevent partial liquid residual from staying between the sampler 400 and the first independent individual element 340 caused by capillarity when mixing the sample and the first reagent 320. Preferably, detect the unfilled detection zone to be a background value at this time.

Following the description above in accordance with the present invention, the line perpendicular with the horizontal line is defined 0 degree. Please refer to FIG. 10C in combination. Rotate the reaction vessel assembly 30 to let the sample and the first reagent 320 mix to form a first mixed liquid 322 in the first independent individual element 340 in step S910. More specifically, the sample and the first reagent 320 are mixed in the capacity zone 341 of the first independent individual element. Preferably, the rotation angle of the reaction vessel assembly is 30 degrees to 55 degrees in clockwise direction. More preferably, the rotation angle is 40 degrees in clockwise direction.

Following the step S920, shake the reaction vessel assembly 30 at an original point. More specifically, after rotating a specific angle of the reaction vessel assembly 30 in the step S910, set that point to be an original point for slightly shaking clockwise and counterclockwise alternately so as to let the sample and the first reagent 320 completely react. To be noticed, there may have partial residual of the first reagent 320 on the distal end 390a of the body 372. Since the reservoir 370 is not fixed in the casing 310 of the reaction vessel assembly 30, the partial residual of the first reagent 320 on the distal end 390a of the body 372 can be dropped down by the centrifugal force when the reaction vessel assembly 30 shaking at the original point.

Figure 10D:
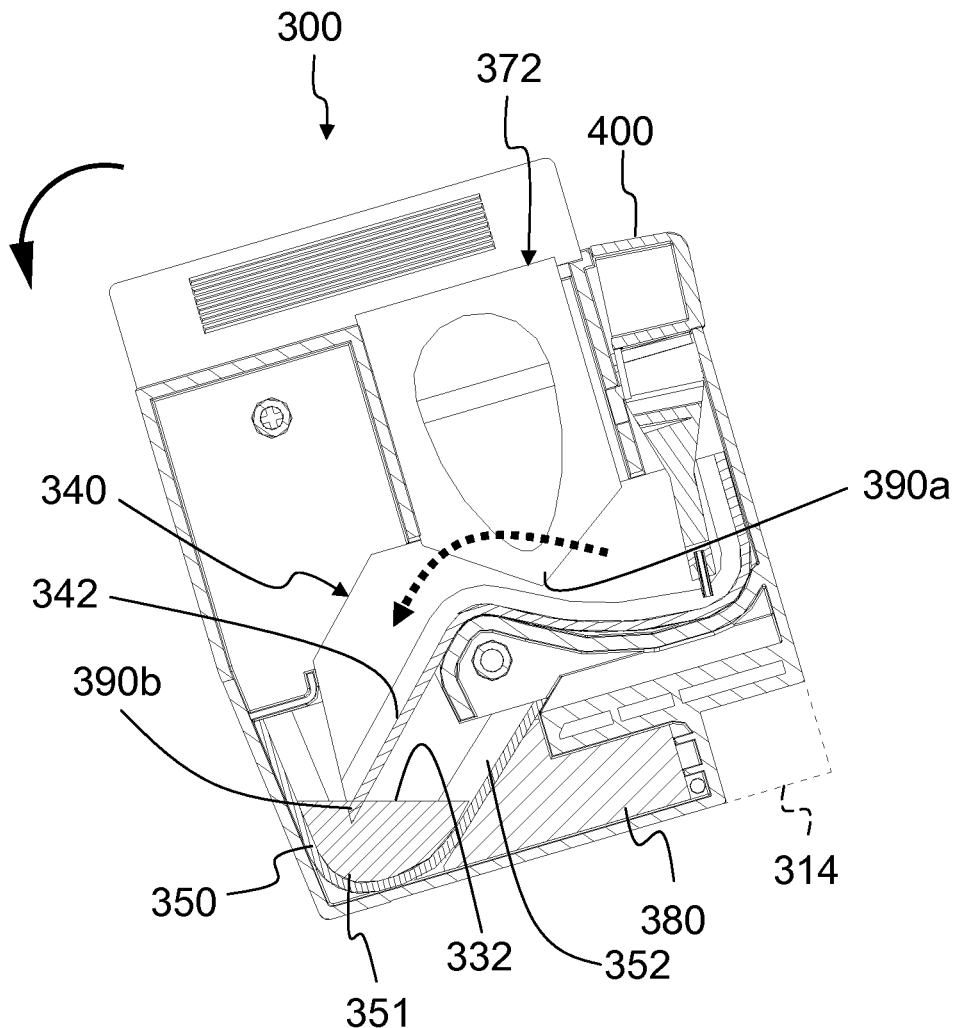

Following the description above, please refer to FIG. 10D in combination. Rotate the reaction vessel assembly 30 to let the first mixed liquid 322 and the second reagent 330 mix to form a second mixed liquid 332 in the second independent individual element 350 in step S930. More specifically, the first mixed liquid 322 and the second reagent 330 are mixed in the capacity zone 351 of the second independent individual element. Preferably, the rotation angle of the reaction vessel assembly is 50 degrees to 75 degrees in counterclockwise direction. More preferably, the rotation angle is 60 degrees in counterclockwise direction. More specifically, the first mixed liquid 322 is flowing into the second independent individual element 350 through the flow channel 342 of the first independent individual element 340 by counterclockwise rotation. Preferably, the second reagent 330 is a dried form reagent disposed on the inner wall of the second independent individual element 350 so that the first mixed liquid 322 flowing into the capacity zone 351 of the second independent individual element 350 will dissolve the second reagent 330 therein. To be noted, when the first mixed liquid 322 was flowing through the flow channel 342 of the first independent individual element 340 (as the boldface arrowhead of the dotted line in FIG. 10D shown), the liquid level of the first mixed liquid 322 will contact with the distal end 390a of the body 372 of the reservoir to bring the residual liquid on the distal end 390a away.

Following the step S940, shake the reaction vessel assembly 30 on an original point. More specifically, after rotating a specific angle of the reaction vessel assembly 30 in the step S930, set that point to be an original point for slightly shaking clockwise and counterclockwise alternately so as to let the first mixed liquid 322 and the second reagent 330 completely react.

Figure 10E:
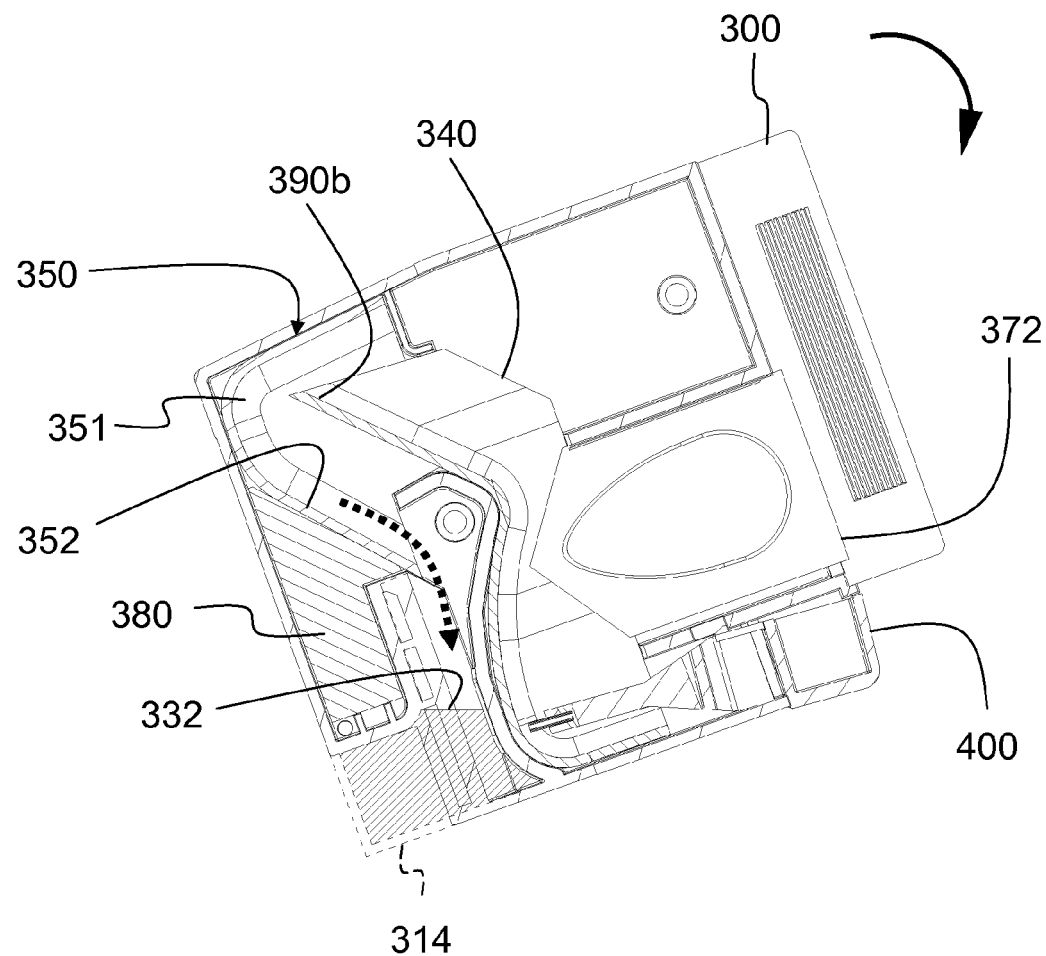

Following the description above, please refer to FIG. 10E in combination. Rotate the reaction vessel assembly 30 to let the second mixed liquid 332 flow into a detection zone 314 in step S950. Preferably, the rotation angle is 60 degrees to 85 degrees in clockwise direction. More preferably, the rotation angle is 70 degrees in clockwise direction. More specifically, the second mixed liquid 332 is flowing into the detection zone 314 of the casing 310 through the flow channel 352 of the second independent individual element 350 by clockwise rotation. To be noticed, when the second mixed liquid 332 is flowing through the flow channel 352 of the second independent individual element 350, the liquid level of the second mixed liquid 332 will contact with the distal end 390b of the first independent individual element 340 to bring the residual liquid on the distal end 390b away.

Following the step S960, analyze the analyte concentration. More specifically, analyze the analyte when the second mixed liquid 332 has been filled in the detection zone 314. Preferably, the analysis is optical measurement and the analyte is glycosylated hemoglobin. In other words, when the detection zone 314 filled with the second mixed liquid 332, perform the optical measurement to obtain a detection value of the glycosylated hemoglobin. Preferably, the detection value was subtracted the background value which detected when the detection zone is empty so as to obtain a more accuracy test result. Preferably, after finished the measurement, rotate the reaction vessel assembly in clockwise direction to let the second mixed liquid 332 absorbed by the absorptive material 380 so as to prevent the contamination caused by leaking liquid when take out the reaction vessel assembly 30 from the detecting instrument.

Although possible types of the reaction vessel, assay device, and measuring method in accordance with the present invention has been described in the embodiment above, those skilled in the art shall recognize that the reaction vessel can be designed differently. Therefore, the spirit of the present invention shall not be limited to these possible types of reaction vessel in accordance with the present invention. In other words, the flow channel forming in the independent individual element instead of forming by the casings pasting can help to take the partial liquid residual on the distal end away when test performing is the key spirit and scope of the present invention. The followings are some other embodiments in accordance with the present invention for those skilled in the art to know more about the spirit of the present invention.

According to the embodiment of the present invention in FIG. 1A, the sample is mixed with the reagent. More specifically, the mixed reaction is a biochemical reaction which is one choice of an embodiment of the present invention. In accordance with the other embodiment, the mixed reaction of the sample and the reagent can be a physical reaction, a chemical reaction, a biological reaction, or a synthetic reaction including the reactions described above. For example, shaking the reaction vessel assembly on the original point is a physical reaction, and the antibody of the reagent combined with the antigen of the sample to proceed the immunological agglutination is a biochemical reaction.

According to the embodiment of the present invention in FIG. 2A, the sampler 400 further comprises the capillary tube 410 used for drawing the sample, but the present invention shall not be limited for this. In accordance with the other embodiment, the sampler can be the other way to obtain the sample such as dropping or importing the sample for instance.

According to the embodiment of the present invention in FIG. 3, the reaction vessel 300 comprises the casing 310, the reagent, and the independent individual element. The casing 310 comprises the bottom casing 311 and the top casing 312, and the shape of the casing is square as FIG. 3 shown, but the present invention shall not be limited for this. In accordance with the other embodiment, the casing can be any other shape such as round shape for instance.

According to the aspect of the present invention as described above, the casing has the opening 313, and the opening is preferably formed on the edge of the casing 310 used for introducing a sample, but the present invention shall not be limited for this. In accordance with the other embodiment, the opening can be formed on any position of the casing, and those skilled in the art can change the opening position as needed.

Following the description above, the casing 310 further comprises the RFID tag 315 used for identifying the message related with the reaction vessel, but it is one choice of an embodiment of the present invention. In accordance with the other embodiment, linear bar code or two-dimensional bar code can replace the RFID tag. In a preferred embodiment of the present invention, the bottom casing 311 has an extending plate relatively protruding from the top casing 312, and the RFID tag or bar code preferably can dispose on the extending plate.

According to the embodiment of the present invention in FIG. 4, the reservoir 370 has the film 371 which preferably can be an aluminum foil, but it is one choice of an embodiment of the present invention. In accordance with the other embodiment, the film can be other metal lamina, and a surface of the film contacted with the first reagent is coated a plastic material so as to adhere with the body 372 in a sealed state. Besides, the way of pulling off the film to let the first reagent 320 leave from the body 372 of the reservoir 370 to mix with the sample is one choice of an embodiment of the present invention. In accordance with the other embodiment, there can be other way to break the sealed state of the reservoir such as slicing or piercing the film for instance.

According to the embodiment of the present invention in FIGS. 5A to 5E, the independent individual element comprises the first independent individual element 340 and the second independent individual element 350, and the independent individual element has the capacity zone which is one choice of an embodiment of the present invention. Those skilled in the art can change the number of the independent individual element and/or the capacity zone depending on the design of the fluid path as needed. Besides, the arc radius of the curved base is R1.0 to RN, in which N is a positive number larger than 1, but the present invention shall not be limited for this. In accordance with the other embodiment, other parts in the independent individual element, such as the flow channel, or the entirety of the individual element can be round.

In accordance with the above embodiment, the first reagent preferably is a liquid form and the second reagent preferably is a dried form, but the present invention shall not be limited for this. In accordance with the other embodiment, the first reagent can be dried form and the second reagent can be liquid form, or the first reagent and the second reagent can both be liquid form or dried form. Those skilled in the art can change the forms of the first reagent and the second reagent as needed.

In accordance with the above embodiment, the first reagent 320 stored in the reservoir 370 and the second reagent 330 disposed on the second independent individual element 350 is one choice of an embodiment of the present invention, and the present invention shall not be limited for this. In accordance with the other embodiment, those skilled in the art can change the reagent placed position, such as the casing or the sampler for instance.

According to the embodiment of the present invention in FIG. 10E, rotating the reaction vessel assembly 30 to let the second mixed liquid 332 flow into a detection zone 314 in step S950 and analyzing the analyte concentration in step S960 is one choice of an embodiment of the present invention, and the present invention shall not be limited for this. In accordance with the other embodiment, the analyte analysis can be performed on the original site where the liquids were blended and no need to transfer the mixed liquid to the detection zone.

In accordance with the above embodiment, the independent individual element is one piece of element separated from the casing 310, but it is one choice of an embodiment of the present invention. In accordance with the other embodiment, the independent individual element can manufacture integrally with the casing 310 in one piece so as to resolve the issue that the residual liquid attached on the reaction vessel by the casings pasting.

Accordingly, the reaction vessel comprises at least an independent individual element integrally formed with the flow channel to solve the issue that the residual liquid attached in the reaction vessel caused by the straight angle or the excess glue which forming by the casings pasting. Furthermore, there are also other advantages in some embodiments of the present invention exemplarily listed as follows:

1. The reaction vessel in accordance with the present invention comprising at least one independent individual element integrally formed with the flow channel is used for taking the residual liquid on the channel terminal away so as to reduce the inappropriate residual liquid volume in the reaction vessel.

2. The independent individual element of the reaction vessel in accordance with the present invention can pretreat to coat with the reagent and individually save in an appropriate circumstance for the reagent so as to prolong the reagent efficiency.

3. The reservoir of the reaction vessel in accordance with the present invention is not fixed in the casing which has an advantage to increase the centrifugal force on the distal end by the shaking so as to facilitate the liquid blending and remove the residual liquid on the distal end 4. The sampler of the assay device in accordance with the present invention does not completely contact with the inner wall of the casing to prevent partial liquid residual from staying in the narrow space caused by the capillarity.

5. The reaction vessel, assay device, and measuring method in accordance with the present invention efficiently controls the variation of the liquid volume in each steps by the independent individual element so as to elevate the accuracy of the test results.

More exemplary embodiments and advantages of the present invention may be ascertained by reviewing the present disclosure and the accompanying drawing. It is intended that the description and embodiments with reference to the accompanying drawing to be considered as exemplary only.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Other embodiments of the invention will appear to those skilled in the art from consideration of the specification and practice of the invention disclosed herein. It is intended that the specification and examples to be considered as exemplary only, with a true scope and spirit of the invention being indicated by the following claims.

What is claimed is:

1. A reaction vessel for analysis of a sample containing an analyte to be determined, which comprises:
   a casing comprising
      an opening formed on the casing and used for introducing the sample; and
      a detection zone disposed at a corner of the casing and used for detecting the analyte;
   a first reagent for mixing with the sample; and
   at least an independent individual element individually separating from the casing and providing a space and a flow channel for receiving the sample and the first reagent;
   wherein the sample and the first reagent are mixed in the independent individual element, and then the analyte is detected in the detection zone.

2. The reaction vessel as claimed in claim 1, further comprising a reservoir which comprises a body and a film, the film used for letting the first reagent stored in the body in a sealed state, and the thickness of the reservoir is less than the opening of the casing, wherein one end of the reservoir is inserted in the independent individual element.

3. The reaction vessel as claimed in claim 2, wherein the casing further comprises a secured element and a limiting element, and the secured element is engaged with the independent individual element to secure the independent individual element and prevent the independent individual element from shaking in the casing, and the limiting element cooperates with the secured element to limit the movement or shake of the independent individual element, and the reservoir is restricted by the limiting element with limitary shake.

4. The reaction vessel as claimed in claim 1, wherein the detection zone is a transparent region to let a light transmit for detecting the analyte and the thickness of detection zone is 2 millimeter (mm) to 10 mm.

5. The reaction vessel as claimed in claim 1, further comprising a sampler and a tilted element, and the sampler having a capillary tube used for drawing the sample, and the tilted element to prevent the sampler from contacting the an inner wall of the casing when the sampler is inserted into the casing.

6. The reaction vessel as claimed in claim 1, further comprising a RFID tag disposed on an outside of the casing and used for identifying a message related with the reaction vessel.

7. The reaction vessel as claimed in claim 1, wherein the reaction vessel is used for detecting a biochemical analyte.

8. The reaction vessel as claimed in claim 7, wherein the biochemical analyte is glycosylated hemoglobin.

9. The reaction vessel as claimed in claim 1, wherein the independent individual element is adjacent to a side wall of the casing.

10. The reaction vessel as claimed in claim 1, wherein the independent individual element is formed integrally and comprises a capacity zone, a flow channel and a distal end, and the capacity zone accommodates the sample and the first reagent which are mixed to form a first mixed liquid, and the flow channel is used for allowing the first mixed liquid flow through.

11. The reaction vessel as claimed in claim 10, wherein the capacity zone has a curved base, and the arc radius of the curved base is R1.0 to RN, in which N is a positive number larger than 1, and the flow channel has an inclined plane with an inclined angle relative to a horizontal plan, which is between 30 degrees to 90 degrees.

12. The reaction vessel as claimed in claim 10, further comprising a second reagent for mixing with the first mixed liquid to form a second mixed liquid.

13. The reaction vessel as claimed in claim 12, wherein the first reagent is a liquid form and the second reagent is a dried form, and the sample is blood, and the viscosities of the first mixed liquid and the second mixed liquid are below 5 cP.

14. The reaction vessel as claimed in claim 12, further comprising a second independent individual element having a space and a flow channel for receiving the second mixed liquid, wherein the distal end of the independent individual element is inserted in the space of the second independent individual element.

15. The reaction vessel as claimed in claim 1, further comprising an absorptive material adjacent to the detection zone and used for absorbing the sample and the first reagent after interaction.

16. A biochemical assay device for analysis a sample containing an analyte to be determined, which comprising:
 a reaction vessel assembly comprising
  a sampler used for drawing the sample; and
  a reaction vessel comprising
   a casing comprising an opening and a detection zone, the opening formed on the casing and used for inserting the sampler, and the detection zone disposed at a corner of the casing and used for detecting the analyte;
   a first reagent stored in a reservoir in a sealed state and used for mixing with the sample to form a first mixed liquid;
   a second reagent used for mixing with the first mixed liquid to form a second mixed liquid;
   a first independent individual element adjacent to a side wall of the casing and providing a space and a flow channel for the sample and the first reagent to be mixed to form the first mixed liquid; and
   a second independent individual element adjacent to an another side wall of the casing and receiving the second reagent and providing a space and a flow channel for the first mixed liquid and the second reagent to be mixed to form the second mixed liquid, wherein one end of the first independent individual element is inserted in the space of the second independent individual element; and
 a detecting instrument used for detecting the analyte in the reaction vessel assembly, and comprising a slot, a rotation element and a light detector, and the slot providing a space for inserting the reaction vessel assembly in the detecting instrument, and the rotation element rotating the reaction vessel assembly to let the sample, the first reagent and the second reagent mixed in the first independent individual element and the second independent individual element, and the light detector used for proceeding optical measurement so as to analyze the analyte concentration in the detection zone.

* * * * *